United States Patent
Kuo

(10) Patent No.: US 11,065,293 B2
(45) Date of Patent: *Jul. 20, 2021

(54) PHARMACEUTICAL COMPOSITION FOR DECREASING THE SIDE EFFECTS OF CANCER DRUG, AND MANUFACTURING METHOD AND USES THEREOF

(71) Applicant: Dai-Ming Kuo, New Taipei (TW)

(72) Inventor: Dai-Ming Kuo, New Taipei (TW)

( * ) Notice: Subject to any disclaimer, the term of this patent is extended or adjusted under 35 U.S.C. 154(b) by 614 days.

This patent is subject to a terminal disclaimer.

(21) Appl. No.: 15/285,846

(22) Filed: Oct. 5, 2016

(65) Prior Publication Data

US 2017/0360866 A1  Dec. 21, 2017

(30) Foreign Application Priority Data

Jun. 15, 2016 (TW) ................................. 105118779

(51) Int. Cl.

| | | |
|---|---|---|
| *A61K 36/88* | (2006.01) | |
| *A61K 36/05* | (2006.01) | |
| *A61K 33/26* | (2006.01) | |
| *A61K 33/06* | (2006.01) | |
| *A61K 31/722* | (2006.01) | |
| *A61K 33/20* | (2006.01) | |
| *A61K 31/122* | (2006.01) | |
| *A61K 31/375* | (2006.01) | |
| *A61K 36/79* | (2006.01) | |
| *A61K 36/899* | (2006.01) | |
| *A61K 36/484* | (2006.01) | |
| *A61K 36/42* | (2006.01) | |
| *A61K 36/185* | (2006.01) | |
| *A61K 36/8994* | (2006.01) | |
| *A61K 36/8969* | (2006.01) | |
| *A61K 36/62* | (2006.01) | |
| *A61K 36/15* | (2006.01) | |
| *A61K 36/428* | (2006.01) | |
| *A61K 36/8968* | (2006.01) | |
| *A61K 36/06* | (2006.01) | |
| *A61K 36/02* | (2006.01) | |
| *A61K 36/062* | (2006.01) | |
| *A61K 36/07* | (2006.01) | |
| *A61K 36/074* | (2006.01) | |
| *A61K 36/18* | (2006.01) | |
| *A61K 36/21* | (2006.01) | |
| *A61K 36/254* | (2006.01) | |
| *A61K 36/284* | (2006.01) | |
| *A61K 36/287* | (2006.01) | |
| *A61K 36/31* | (2006.01) | |
| *A61K 36/344* | (2006.01) | |
| *A61K 36/41* | (2006.01) | |
| *A61K 36/46* | (2006.01) | |
| *A61K 36/48* | (2006.01) | |
| *A61K 36/481* | (2006.01) | |
| *A61K 36/537* | (2006.01) | |
| *A61K 36/638* | (2006.01) |
| *A61K 36/748* | (2006.01) |
| *A61K 36/87* | (2006.01) |
| *A61K 45/06* | (2006.01) |

(52) U.S. Cl.
CPC ............ *A61K 36/88* (2013.01); *A61K 31/122* (2013.01); *A61K 31/375* (2013.01); *A61K 31/722* (2013.01); *A61K 33/06* (2013.01); *A61K 33/20* (2013.01); *A61K 33/26* (2013.01); *A61K 36/02* (2013.01); *A61K 36/05* (2013.01); *A61K 36/06* (2013.01); *A61K 36/062* (2013.01); *A61K 36/07* (2013.01); *A61K 36/074* (2013.01); *A61K 36/15* (2013.01); *A61K 36/18* (2013.01); *A61K 36/185* (2013.01); *A61K 36/21* (2013.01); *A61K 36/254* (2013.01); *A61K 36/284* (2013.01); *A61K 36/287* (2013.01); *A61K 36/31* (2013.01); *A61K 36/344* (2013.01); *A61K 36/41* (2013.01); *A61K 36/42* (2013.01); *A61K 36/428* (2013.01); *A61K 36/46* (2013.01); *A61K 36/48* (2013.01); *A61K 36/481* (2013.01); *A61K 36/484* (2013.01); *A61K 36/537* (2013.01); *A61K 36/62* (2013.01); *A61K 36/638* (2013.01); *A61K 36/748* (2013.01); *A61K 36/79* (2013.01); *A61K 36/87* (2013.01); *A61K 36/899* (2013.01); *A61K 36/8968* (2013.01); *A61K 36/8969* (2013.01); *A61K 36/8994* (2013.01); *A61K 45/06* (2013.01)

(58) Field of Classification Search
CPC ... A61K 31/122; A61K 31/375; A61K 31/722
See application file for complete search history.

(56) References Cited

FOREIGN PATENT DOCUMENTS

JP    2015051970 A   * 3/2015

OTHER PUBLICATIONS

Srivastava et al. Cancer Research. vol. 67, Issue 9 Supplement. Abstract only. (Year: 2007).*
Zhang et al. Frontiers in Pharmacology. Nov. 1, 2018, vol. 9, Article 1253. 25 pages. (Year: 2018).*

* cited by examiner

*Primary Examiner* — Amy L Clark
(74) *Attorney, Agent, or Firm* — Muncy, Geissler, Olds and Lowe, P.C.

(57) ABSTRACT

The present invention provides a pharmaceutical composition comprising a mushroom, a rhizome, a fruit, a leaf, a flower, an alga, an energy-rich liquid, a salt-rich liquid, an assist agent and an anti-oxide agent. Said pharmaceutical composition has ability to protect liver, improve autoimmunity, reduce pain caused by cancer, protect an organ from the side-effects caused by chemical cancer drugs and increase the functions of chemical cancer drugs.

4 Claims, 18 Drawing Sheets

PHARMACEUTICAL COMPOSITION FOR DECREASING THE SIDE EFFECTS OF CANCER DRUG, AND MANUFACTURING METHOD AND USES THEREOF

CROSS-REFERENCE TO RELATED APPLICATIONS

This Non-provisional application claims priority under 35 U.S.C. § 119(a) on Patent Application No(s). 105118779 filed in Taiwan, Republic of China, on Jun. 15, 2016, the entire contents of which are hereby incorporated by reference.

FIELD OF THE INVENTION

The present invention relates to a pharmaceutical composition for treating cancer, especially related to a pharmaceutical composition can combine with chemotherapeutic drugs for treating cancer.

BACKGROUND OF THE INVENTION

Chemotherapy is an important clinical treatment for cancer patients, which is through administering anticancer drugs to patients to kill cancer cells. In comparison with the conventional surgery and radiation therapy, the advantage of chemotherapy is to achieve systemic treatment. Therefore, chemotherapy becomes the major cancer treatment currently, and is the most important treatment for metastatic cancer patients.

The marketed chemotherapeutic drugs can be divided into chemical synthesized drugs and targeted drugs. The chemical synthesized drugs, including Bleomycin, Cisplatin, Fluorouracil (5-FU), Methotrexate, Taxol, are used to attack the cells which divided rapidly. Hence, in addition to cancer cells, the normal cells, such as white blood cells, red blood cells, platelets, hair follicle cells, gastrointestinal epithelial cells, germ cells, are also the object of chemical synthesized drugs. Consequently, chemical synthesized drugs usually causes side effects including nausea, vomiting, bleeding, diarrhea, hair loss, reproductive ability reduce, mucosal damage and inflamed, and make patients become easily infected.

Targeted drugs, including Bevacizumab, Iressa and Erlotinib, are acting on specific antigens or proteins of the cancer cells. Therefore, the targeted drugs are only able to treat the primary site of cancer cells, but not able to treat the metastatic cancer cells. Besides, targeted drugs also cause some side effects such as skin rash, pain, stomatitis, diarrhea, fever, high blood pressure, liver damage and other side effects.

Furthermore, some chemotherapeutic drugs, such as Fluorouracil (5-FU) and Taxol would cause arrhythmia, liver and kidney dysfunction, pain, organ hypertrophy, etc., leading to the life quality decrease of cancer patient. Therefore, it is important to develop a drug to reduce the side effects of chemotherapeutic drugs and improve their therapeutic efficacy simultaneously.

SUMMARY OF THE INVENTION

Accordingly, the present invention provides a pharmaceutical composition could combine with chemotherapy drugs for treating cancer and has ability to decrease the side effects of cancer drug. Said pharmaceutical composition comprising a mushroom, a rhizome, a fruit, a leaf, a flower, an alga, an energy-rich liquid, a salt-rich liquid, an assist agent and an anti-oxide agent.

Preferably, the mushroom is selected from the group consisting of 24-36 grams of *Phellinus linteus*, 16-24 grams of *Ganoderma lucidum*, 16-24 grams of *Agaricus subrufescens*, 4-6 grams of *Antrodia cinnamomea*, 4-6 grams of Caterpillar fungus and the combination thereof.

Preferably, the rhizome is selected from the group consisting of 16-24 grams of *Rhizoma polygonati*, 8-12 grams of *Astragalus*, 8-12 grams of *Salvia miltiorrhiza*, 8-12 grams of *Codonopsis pilosula*, 12-18 grams of *Hedyotis diffusa*, 12-18 grams of *Eucommia ulmoides*, 8-12 grams of *Atractylodes macrocephala*, 8-12 grams of *Radix trichosanthis*, 8-12 grams of *Eleutherococcus senticosus*, 8-12 grams of *Ophiopogon japonicas* 8-12 grams of *Rhodiola*, 2.4-3.6 grams of Peeled Licorice and the combination thereof.

Preferably, the fruit is selected from the group consisting of 12-18 grams of Job's Tears, 8-12 grams of *Ligustrum lucidum*, 8-12 grams of *Schisandra chinensis*, 9.6-14.4 grams of Germinated brown rice, 8-12 grams of lotus seed, 8-12 grams of Black sesame, 8-12 grams of Corn Silk, 8-12 grams of *Siraitia grosvenorii*, 1.6-2.4 grams of powder extract from red grape skin and the combination thereof.

Preferably, the leaf is selected from the group consisting of 8-12 grams of spinach, 8-12 grams of germinated Broccoli, 8-12 grams of papaya leaf, 6.4-9.6 grams of lotus leaf and the combination thereof.

Preferably, the flower is selected from the group consisting of 8-12 grams of *Chrysanthemum*, 8-12 grams of *Cota tinctoria*, 8-12 grams of *Lonicera Japonica*, 8-12 grams of *Matricaria recutita* (Chamaemomile) and the combination thereof.

Preferably, the alga is selected from the group consisting of 8-12 grams of sea weed, 8-12 grams of sea-tangle, 8-12 grams of kelp and the combination thereof.

Preferably, the energy-rich liquid comprising 4.5 to 5.5 mg of ferric chloride and 200 ml of distilled water.

Preferably, the salt-rich liquid comprising 112.5-137.5 grams of deep sea salt, 27-33 grams of magnesium chloride, 18-22 ml of brine, 0.99-1.21 grams of calcium chloride and 0.495-0.605 grams potassium chloride.

Preferably, the assist agent comprising 18-22 grams of citric acid, 18-22 grams of selenium yeast, 270-330 mg of coenzyme Q10 and 2.7-3.3 grams of vitamin C.

Preferably, the anti-oxide agent comprising 9-11 grams of chitin oligosaccharides, 4.5-5.5 grams of glutathione, 0.9-1.1 grams of pine bark, and 0.9-1.1 grams of Fucoidan.

In one embodiment of the present invention, the pH value of the pharmaceutical composition is 1.2-2. Preferably, the pH value of the pharmaceutical composition is 1.2-1.8.

The present invention further provides a method for prepare a pharmaceutical composition which can reduce the side effects of cancer drug. Said method comprises: adding a traditional chinese medicine into water and concentrating into a solution; adding an energy-rich liquid into the solution, the energy-rich liquid comprising $FeCl_3$ and water; adding a salt-rich liquid into the solution, the salt-rich liquid comprising a deep sea salt, a magnesium chloride, a brine, a calcium chloride and a potassium chloride; adding an assist agent into the solution, the assist agent comprising a citric acid, a selenium yeast, a coenzyme Q10 and a vitamin C; adding an anti-oxide agent into the solution, the anti-oxide agent comprising a chitin oligosaccharide, a glutathione, a pine bark and a fucoidan; Mixing and fermenting the solution; and centrifuging to obtaining a pharmaceutical composition.

Preferably, the traditional chinese medicine comprising a mushroom, a rhizome, a fruit, a leaf, a flower, an alga and the combination thereof.

Preferably, the mushroom is selected from the group consisting of 24-36 grams of *Phellinus linteus*, 16-24 grams of *Ganoderma lucidum*, 16-24 grams of *Agaricus subrufescens*, 4-6 grams of *Antrodia cinnamomea*, 4-6 grams of Caterpillar fungus and the combination thereof; the rhizome is selected from the group consisting of 16-24 grams of *Rhizoma polygonati*, 8-12 grams of *Astragalus*, 8-12 grams of *Salvia miltiorrhiza*, 8-12 grams of *Codonopsis pilosula*, 12-18 grams of *Hedyotis diffusa*, 12-18 grams of *Eucommia ulmoides*, 8-12 grams of *Atractylodes macrocephala*, 8-12 grams of *Radix trichosanthis*, 8-12 grams of *Eleutherococcus senticosus*, 8-12 grams of *Ophiopogon japonicas*, 8-12 grams of *Rhodiola*, 2.4-3.6 grams of Peeled Licorice and the combination thereof; the fruit is selected from the group consisting of 12-18 grams of Job's Tears, 8-12 grams of *Ligustrum lucidum*, 8-12 grams of *Schisandra chinensis*, 9.6-14.4 grams of Germinated brown rice, 8-12 grams of lotus seed, 8-12 grams of Black sesame, 8-12 grams of Corn Silk, 8-12 grams of *Siraitia grosvenorii*, 1.6-2.4 grams of powder extract from red grape skin and the combination thereof; the leaf is selected from the group consisting of 8-12 grams of spinach, 8-12 grams of germinated Broccoli, 8-12 grams of papaya leaf, 6.4-9.6 grams of lotus leaf and the combination thereof; the flower is selected from the group of 8-12 grams of *Chrysanthemum*, 8-12 grams of *Cota tinctoria*, 8-12 grams of *Lonicera Japonica*, 8-12 grams of *Matricaria recutita* (Chamaemomile) and the combination thereof; the alga is selected from the group consisting of 8-12 grams of seaweed, 8-12 grams of sea-tangle, 8-12 grams of kelp and the combination thereof.

In one embodiment of the present invention, the pH value of the pharmaceutical composition is 1.2-2. Preferably, the pH value of the pharmaceutical composition is 1.2-1.8.

Preferably, the fermenting is conduct 3-5 days at room temperature.

The present invention further provides a method for decreasing the side effects from a cancer drug, comprising; applying the pharmaceutical composition of claim 1 to a patient.

Preferably, the pharmaceutical composition has ability to protect liver, increase the immunity, reduce pain, protect an organ from the side effects of cancer drugs or improve the treating effect of the cancer drug.

Preferably, the concentration of the pharmaceutical composition is 25 μl/kg/day-84 μl/kg/day.

Preferably, the application method of the pharmaceutical composition is 3-10 times daily and diluting the pharmaceutical composition to $1/1000$-$3/1000$ times while using.

Preferably, the cancer drug is a chemical synthesized drug or a targeted drug. Said chemical synthesized drug is selected form the group consisting of 5-fluorouracil (5-FU), Taxol, cisplatin, anthracycline, cyclophosphamide and a combination thereof.

Preferably, the organ is heart, liver, kidney or pancreas.

BRIEF DESCRIPTION OF THE DRAWINGS

FIG. 3A illustrate the numbers of the white blood cell. FIG. 3B illustrate the numbers of the lymphatic cell. FIG. 3C illustrate the numbers of the monocyte. FIG. 3D illustrate the numbers of the granulocyte. FIG. 3E illustrate the numbers of the platelet.

FIG. 4A illustrate the numbers of the white blood cell. FIG. 4B illustrate the numbers of the lymphatic cell. FIG. 4C illustrate the numbers of the monocyte. FIG. 4D illustrates the numbers of the granulocyte. FIG. 4E illustrate the numbers of the platelet.

FIG. 5A illustrate the expression of human cytokine IL-8. FIG. 5B illustrate the expression of human cytokine IL-6. FIG. 5C illustrate the expression of human cytokine IL-1RA.

FIG. 5D illustrate the expression of human cytokine TNF-α. FIG. 5E illustrate the expression of murine cytokine IL-12. FIG. 5F illustrate the expression of murine cytokine IL-12. FIG. 5G illustrates the expression of human cytokine IL-12.

FIG. 6A illustrate the expression of human cytokine IL-6. FIG. 6B illustrate the expression of human cytokine TNF-α. FIG. 6C illustrate the expression of murine cytokine G-CSF. FIG. 6D illustrates the expression of human cytokine IL-12.

FIG. 8A illustrates the heart weight.
FIG. 8B illustrates the liver weight.
FIG. 8C illustrates the pancreas weight.
FIG. 8D illustrates the kidney weight.

DETAILED DESCRIPTION OF THE INVENTION

Figure 1A:
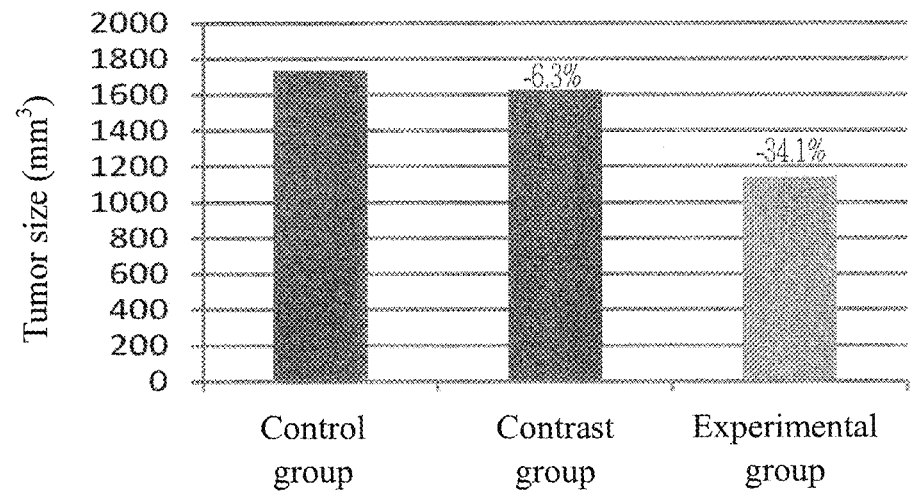
FIG. 1A illustrates the tumor size after 14 days treatment.

1. The Preparation of the Presented Pharmaceutical Composition

First, the condensed solution was prepared by one or several materials of traditional chinese medicine list in Table 1. The preparation process comprising: (1) six times more amount of water was added into the 360 grams of traditional chinese medicine to made a 2160 mL solution; (2) the 2160 ml solution was condensed as 1200 mL by reduce pressure under high temperature (about 70° C.); (3) kept the condensed solution stable and cool, and removed 5% precipitate after two days to obtain a condensed solution.

TABLE 1

The traditional chinese medicine of the pharmaceutical composition of the present invention

| items | Chinese medicine raw materials | weight |
|---|---|---|
| mushroom | *Phellinus linteus* | 30 g |
| | *Ganoderma lucidum* | 20 g |
| | *Agaricus subrufescens* | 20 g |
| | *Antrodia cinnamomea* | 5 g |
| | Caterpillar fungus | 5 g |
| rhizome | *Rhizoma polygonati* | 20 g |
| | *Astragalus* | 10 g |
| | *Salvia miltiorrhiza* | 10 g |
| | *Codonopsis pilosula* | 10 g |

TABLE 1-continued

The traditional chinese medicine of the pharmaceutical composition of the present invention

| items | Chinese medicine raw materials | weight |
|---|---|---|
| | Hedyotis diffusa | 15 g |
| | Eucommia ulmoides | 15 g |
| | Atractylodes macrocephala | 10 g |
| | Radix trichosanthis | 10 g |
| | Eleutherococcus senticosus | 10 g |
| | Ophiopogon japonicus | 10 g |
| | Rhodiola | 10 g |
| | Peeled Licorice | 3 g |
| fruit | Job's Tears | 15 g |
| | Ligustrum lucidum | 10 g |
| | Schisandra chinensis | 10 g |
| | Germinated brown rice | 12 g |
| | Lotus seed | 10 g |
| | Black sesame | 10 g |
| | Corn Silk | 10 g |
| | Siraitia grosvenorii | 10 g |
| | Powder Extract from Red Grape Skin | 2 g |
| leaf | Spinach | 10 g |
| | Germinated Broccoli | 10 g |
| | Papaya leaf | 10 g |
| | Lotus leaf | 8 g |
| flower | Chrysanthemum | 10 g |
| alga | Sea Weed | 10 g |

Then, an energy-rich liquid, a salt-rich liquid, an assist agent and an anti-oxide agent were added sequentially into above mentioned 200 mL condensed solution which contains 60 grams of solid precipitate. After mixing, the solution was fermented at room temperature (25° C.) for 3-7 days. Preferably, fermentation is conduct 3 days. Said energy-rich liquid comprising 5 mg of ferric chloride ($FeCl_3$) and 200 ml of distilled water. Said salt-rich liquid comprising 125 grams of deep sea salt, 30 grams of magnesium chloride, 20 mL brine, 1.1 grams of calcium chloride ($CaCl_2$) and 0.55 grams of potassium chloride (KCL). Said assist agent comprising 20 grams of citric acid, 20 grams of selenium yeast, 10% concentration 300 mg of coenzyme Q10 and 3 grams of vitamin C. Said antioxidant comprising 70% concentration 10 grams of chitin oligosaccharides, 98% concentration 5 grams of glutathione, 80% concentration 1 g of pine bark and 80% concentration 1 gram of fucoidan.

The distilled water was added into the above-mentioned fermented solution to make a total volume of solution is 500 mL. After stirring, kept solution stable for 1 day and then centrifuged at 1500 rpm for 15 minutes. The supernatant is the pharmaceutical compositions of the present invention, which contains 25% deep sea salt, 6% magnesium chloride. The pH value of the pharmaceutical composition is 1.5±0.3 in order to maintain the product stability.

2. The Effect of the Presented Pharmaceutical Compositions on Tumor Growth 7-week-old male mice (20-24 grams, CB17/Icr-Prkdcscid/IcrIcoCrlBltw) was subcutaneously inoculated with $3 \times 10^6$ HT-29 colon cancer cells or $1 \times 10^7$ A549 lung adenocarcinoma cells, leading to colon cancer or lung adenocarcinoma. HT-29 colon cancer cells and A549 lung adenocarcinoma cells are dissolve in 100 µL PBS contains 50% matrigel, respectively. While the volume of tumors is grown to 200 mm³, the male mice were divided into three groups including: (a) control group, do not give any medication on day 0 to day 14; (b) contrast group, give the chemotherapeutic agent 5-FU (100 mg/kg) or cisplatin (4 mg/kg) only on the day 0 and day 7; and (c) experimental group, administered the presented pharmaceutical composition continuously for 21 days. The presented pharmaceutical composition was administered 7 days before the give chemotherapeutic agent. The administered method is twice daily, and each dose is 0.5-1.67 µL/mouse. On day 0 and day 7, the chemotherapy drugs 5-FU (100 mg/kg) or cisplatin (4 mg/kg) was administered while the presented pharmaceutical composition was not administered. On day 14 after administered presented pharmaceutical composition, the tumor was acquired and measured its weight.

Figure 1B:
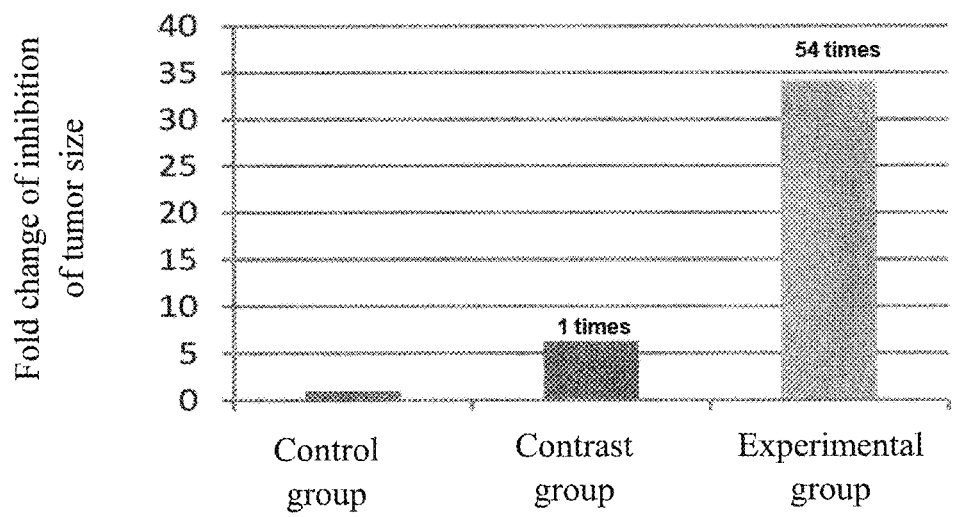
FIG. 1B illustrates the fold change of inhibition of tumor size after 14 days treatment.

Please refer to FIGS. 1A-1B. Compared to control group, the volume of tumor of contrast group is reduce 6.3% in average. The inhibitory ability of contrast group was 1 times higher than the control group. However, the volume of tumor of experimental group can effectively reduce 34.1%. The inhibitory ability of experimental group was 5.4 times higher than the control group. Therefore, the pharmaceutical compositions of the present invention can improve the inhibitory ability of chemotherapeutic agent on tumor.

3. The Effect of the Presented Pharmaceutical Compositions on the Function of Liver Many studies have shown that the cancer cells would flow into the liver through the blood, leading to the liver dysfunction. Thus, the serum of each group in example 2 was collected at day 14 after administered drugs to analyze the expression of alanine aminotransferase (ALT).

Figure 2A:
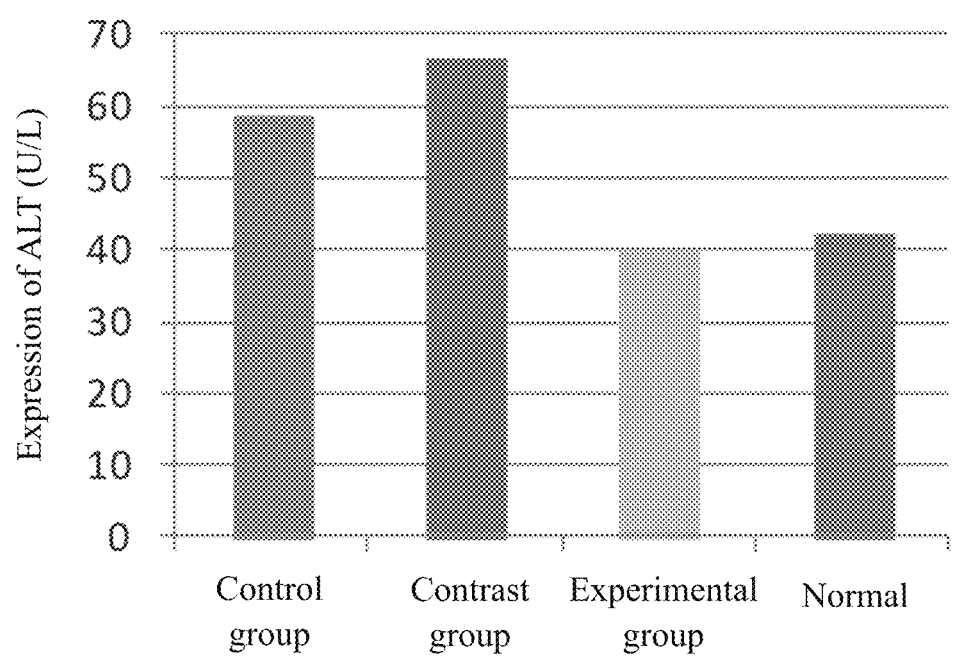
FIG. 2A illustrates the expression of Alanine aminotransferase in the serum after implant the colon cancer cells.

Please refer to FIG. 2A. The rats of normal group were neither implanted colon cancer cells nor administered drugs. Compare with normal group, the ALT concentration of control group was increased. Means that the colon cancer cells would cause liver damage. Compare with control group, the ALT concentration of contrast group was increased. However, the ALT concentration of experimental group was decreased and the expression level is close to the normal group.

Figure 2B:
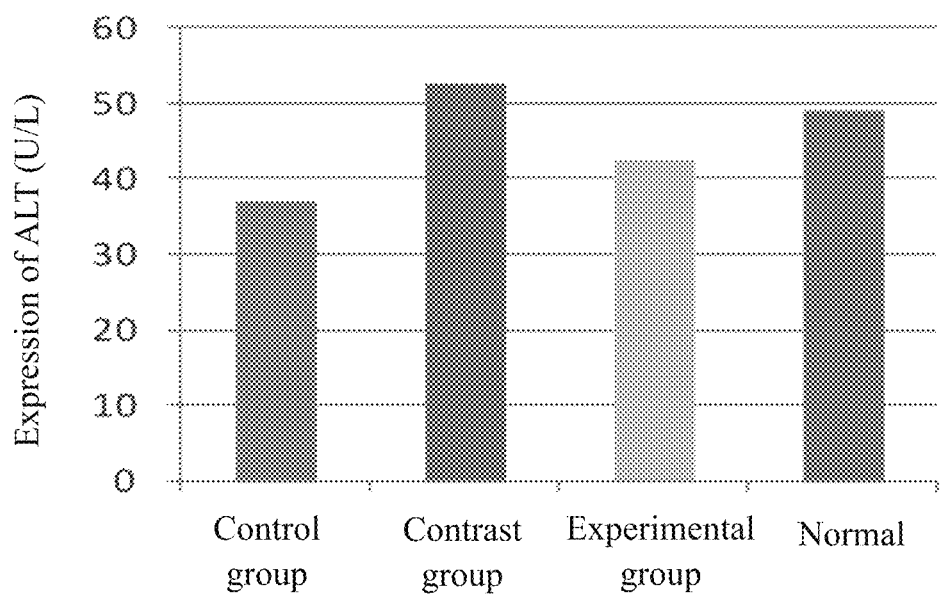
FIG. 2B illustrates the expression of Alanine aminotransferase in the serum after implant the lung adenocarcinoma cells.

Please refer to FIG. 2B. The rats of normal group were neither implant lung adenocarcinoma nor administered drugs. Compare with normal group and control group, the ALT concentration of the contrast group was increased. However, the ALT concentration of experimental group was decreased and the expression level is close to the normal group. Therefore, the chemotherapeutic agent 5-FU and Cisplatin does not protect against liver cancer cell from destroy, but rather to increase the burden on the liver and accelerate liver damage, however, the pharmaceutical compositions of the present invention has a protection function on liver, and maintain normal liver function, in order to increase the effectiveness against cancer cells.

4. The Effect of the Presented Pharmaceutical Compositions on Immune System

It is well known that the immune cells and cytokines are involved in inhibit cancer growth. To understand the effect of presented pharmaceutical compositions on immune system, the blood of each group in example 2 was collected at day 14 after administered drugs to analyze the numbers of immune cells and cytokines.

Figure 3A:
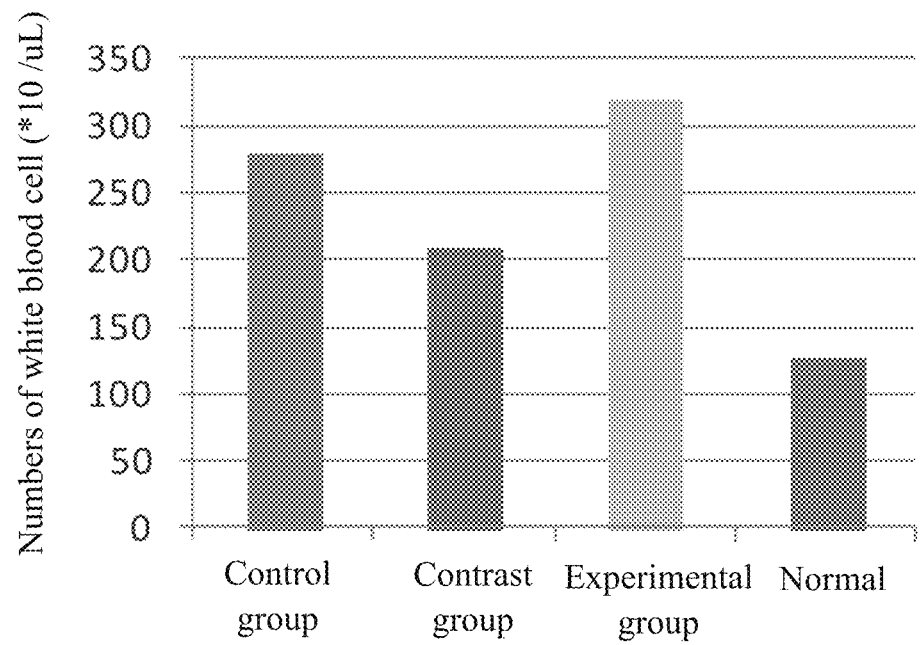
FIGS. 3A-E illustrates the numbers of immune cells in the blood after implant the colon cancer cells.
Figure 3B:
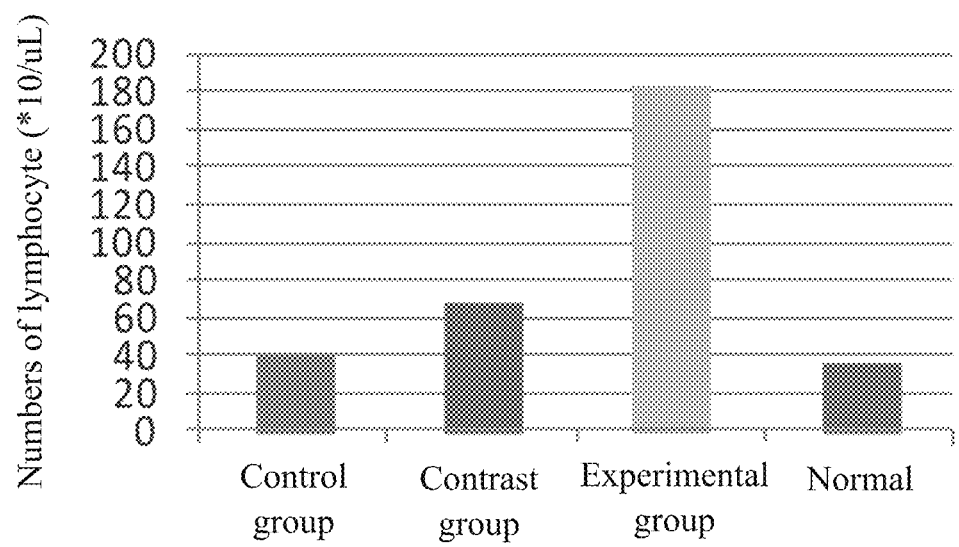
Figure 3C:
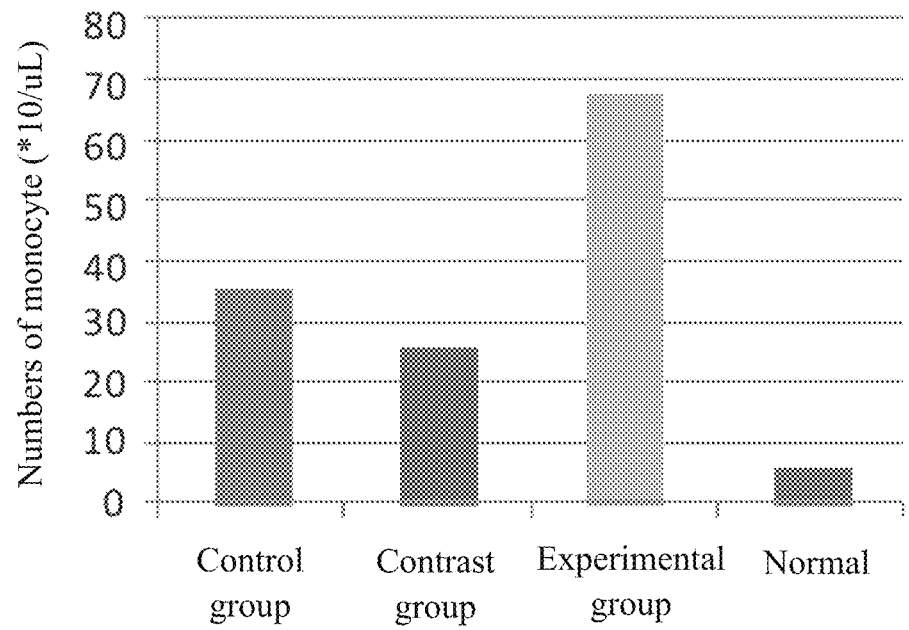
Figure 3D:
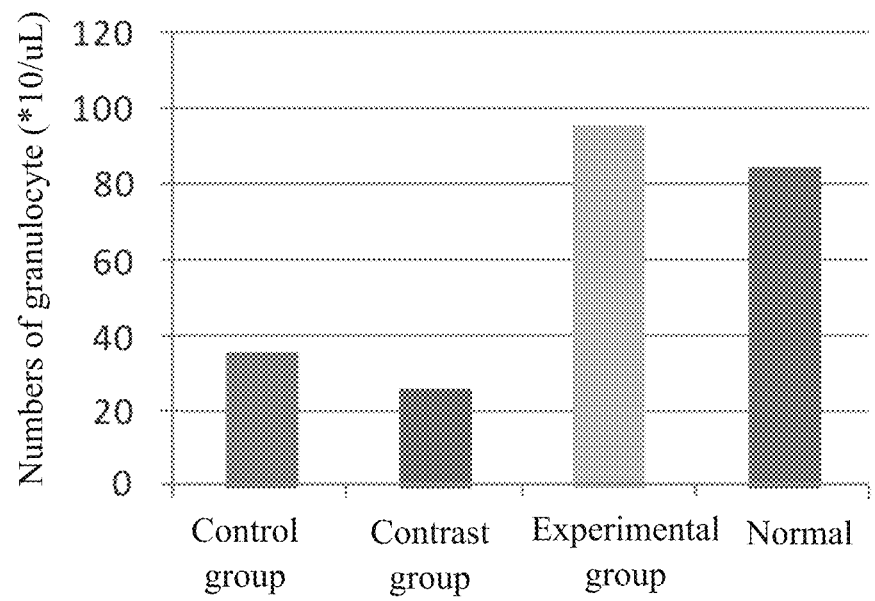
Figure 3E:
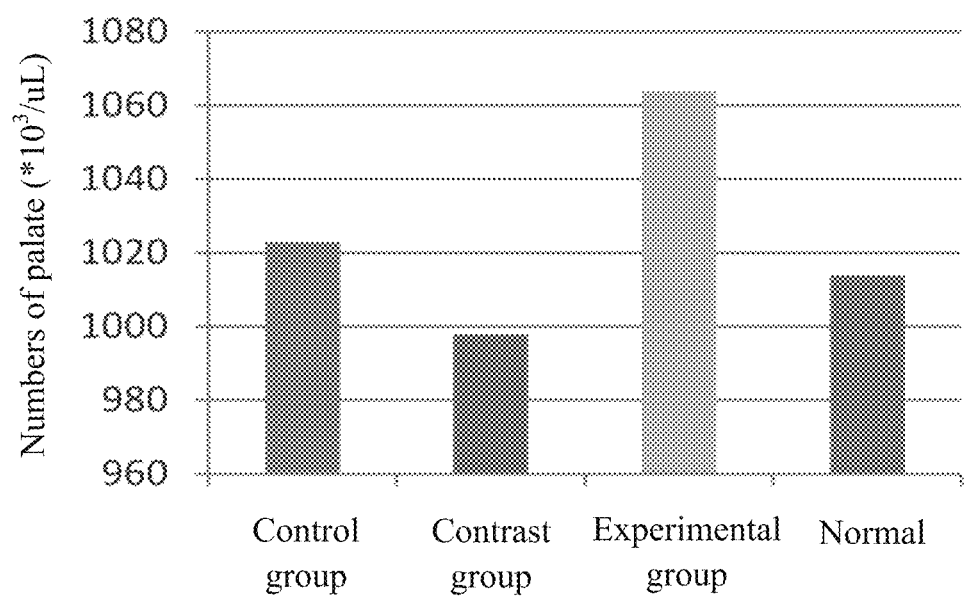

Please refer to FIGS. 3A-3E. The rats of normal group were neither implant colon cancer cells nor administered drugs. Compare with control group and contrast group, present pharmaceutical composition can effectively increase the numbers of white blood cell (FIG. 3A), lymphocyte (FIG. 3B), monocyte (FIG. 3C), granulocyte (FIG. 3D) and platelet (FIG. 3E).

Figure 4A:
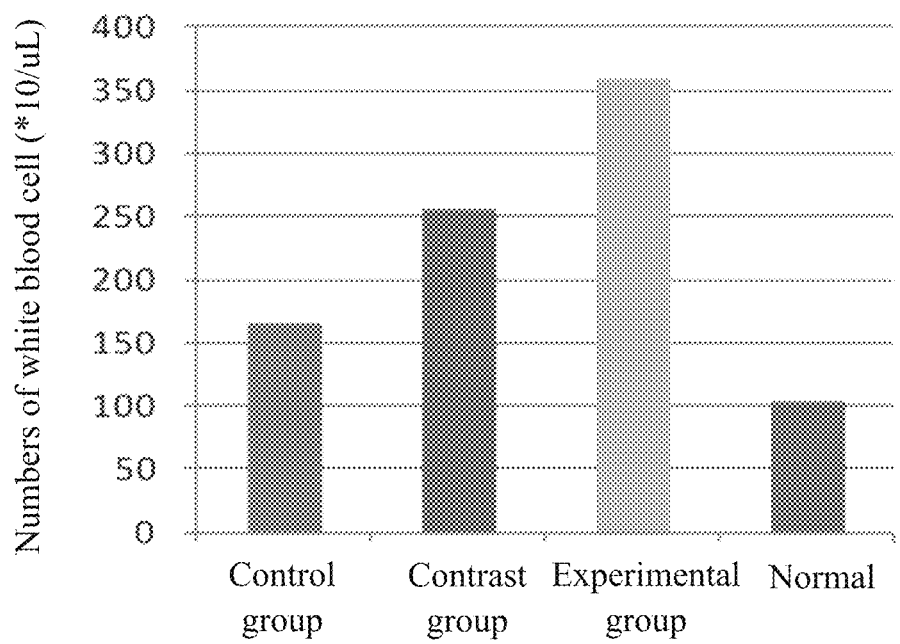
FIGS. 4A-E illustrates the numbers of immune cells in the blood after implant the lung adenocarcinoma cancer cells.
Figure 4B:
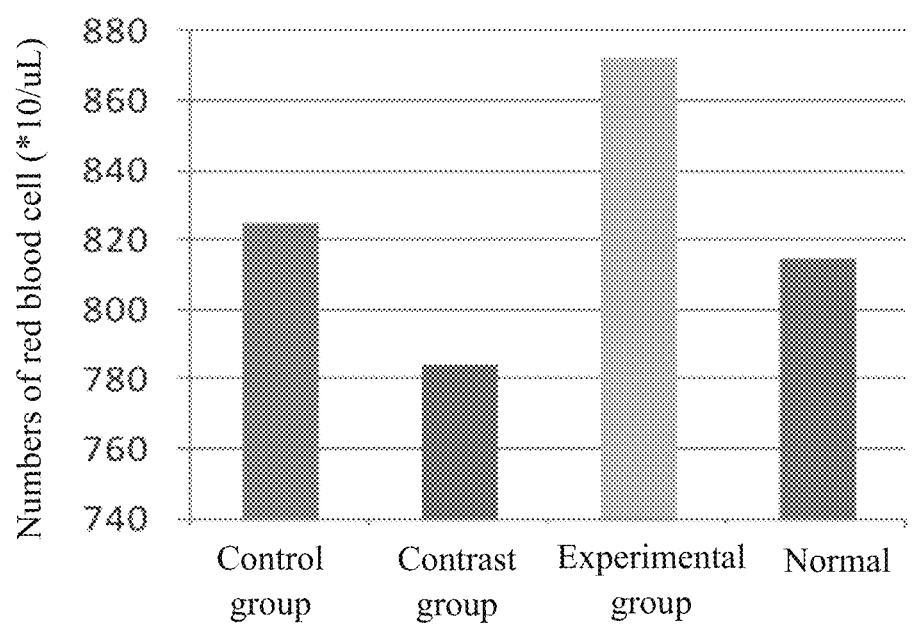
Figure 4C:
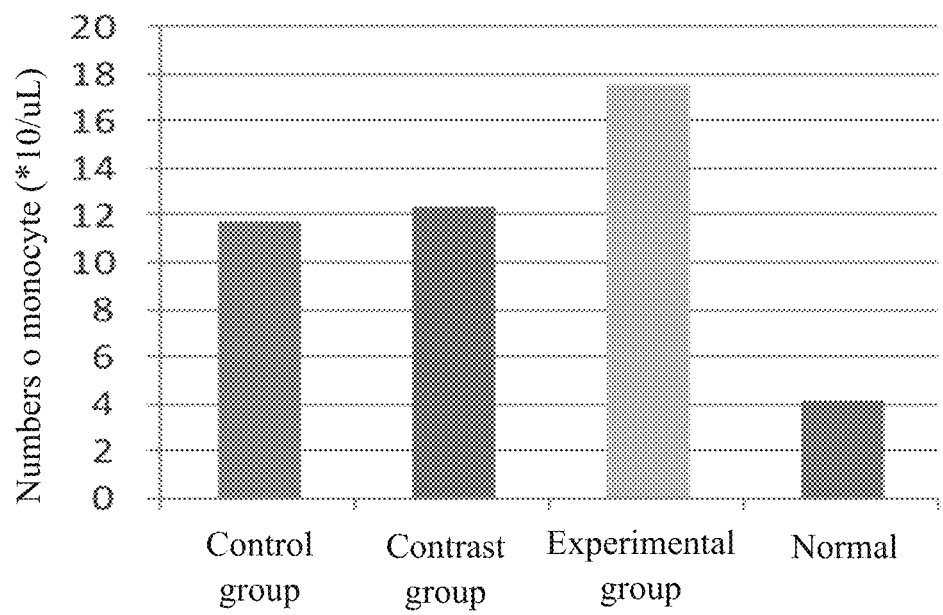
Figure 4D:
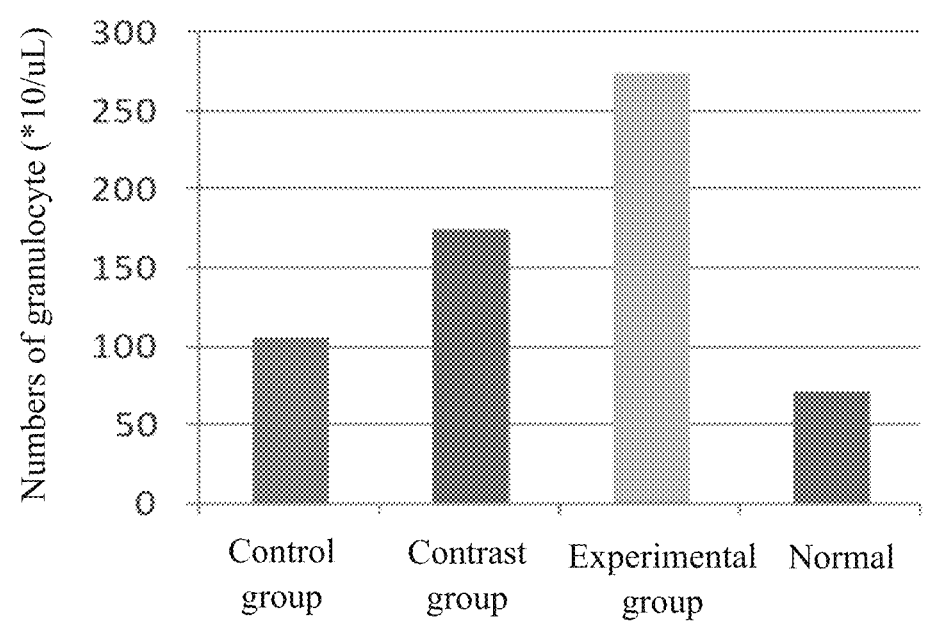
Figure 4E:
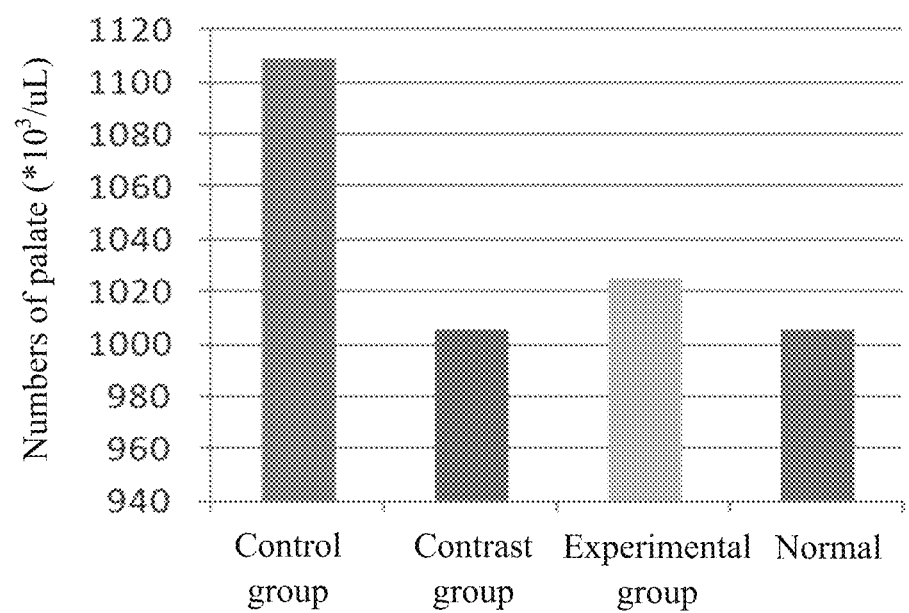

Please refer to FIGS. 4A-4E. The rats of normal group were neither implant with lung adenocarcinoma nor administered drugs. Compare with control group and contrast group, present pharmaceutical composition can effectively increase the numbers of white blood cell (FIG. 4A), Red blood cell (FIG. 4B), monocyte (FIG. 4C), granulocyte (FIG. 4D) and platelet (FIG. 4E).

Figure 5A:
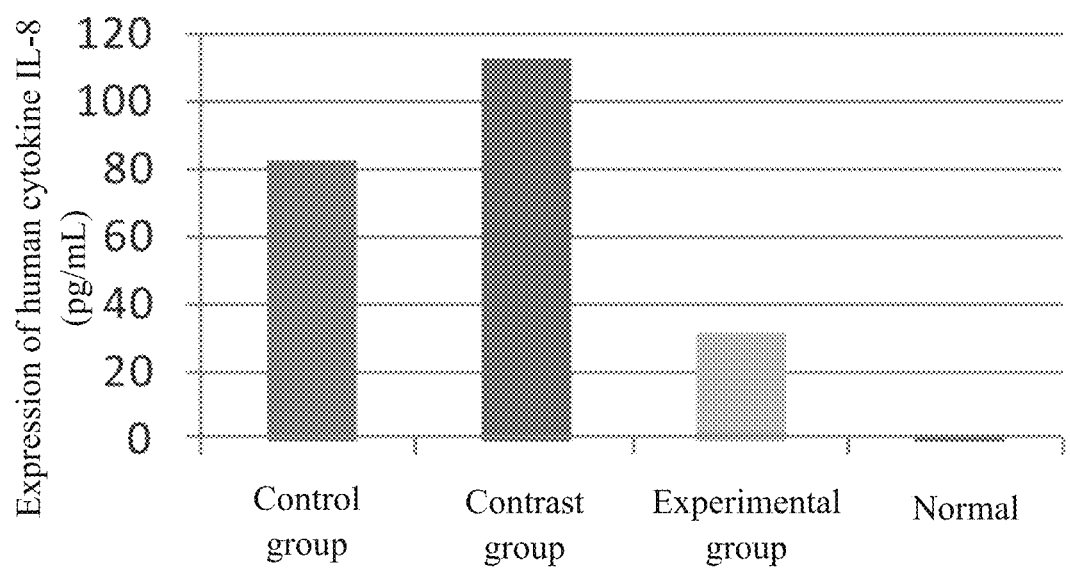
FIGS. 5A-G illustrates the expression of cytokines in the blood after implant the colon cancer cells.
Figure 5B:
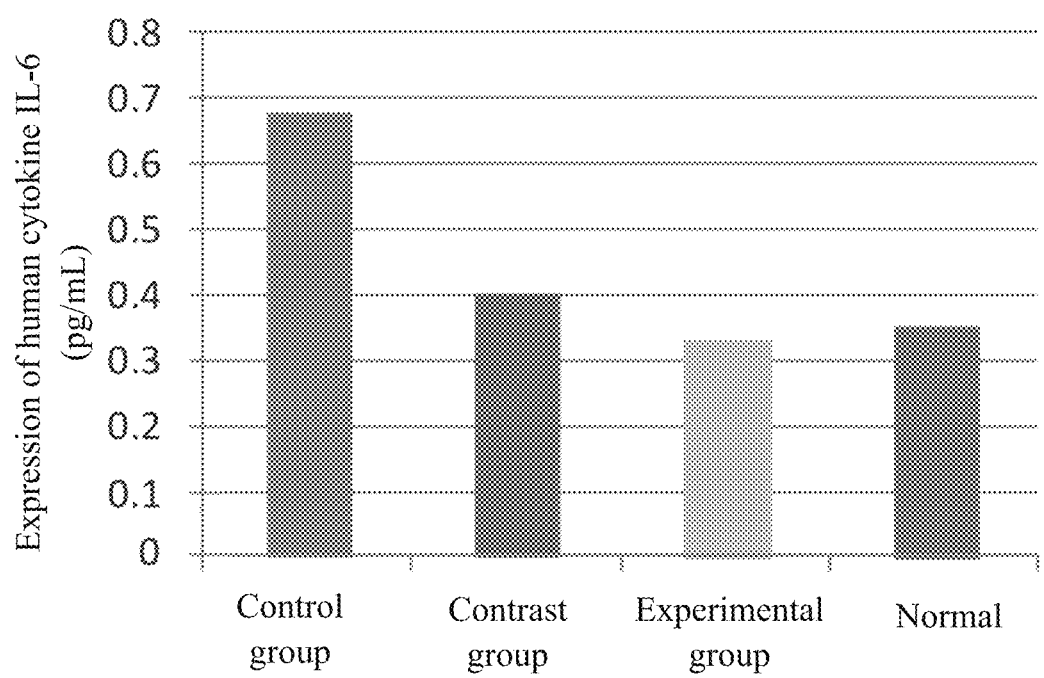
Figure 5C:
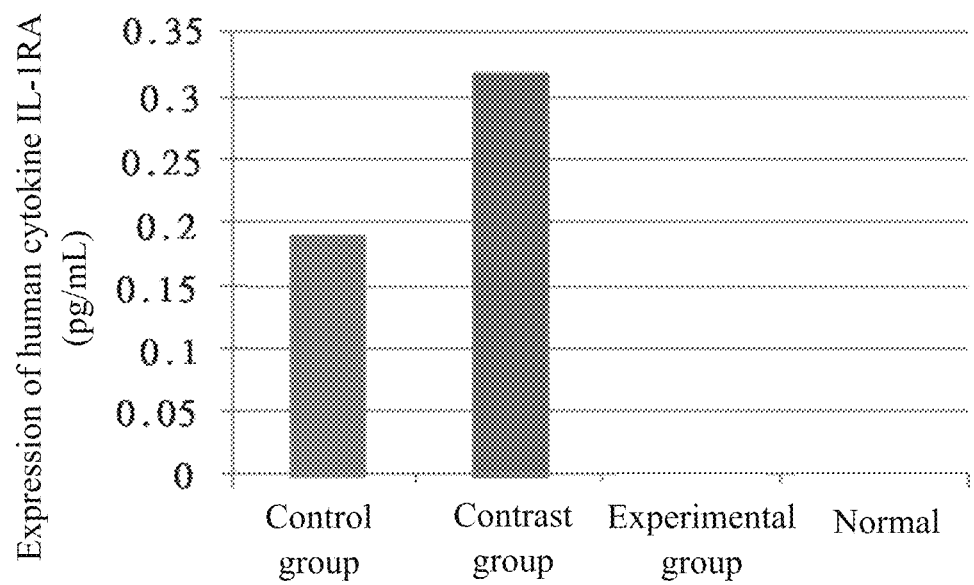
Figure 5D:
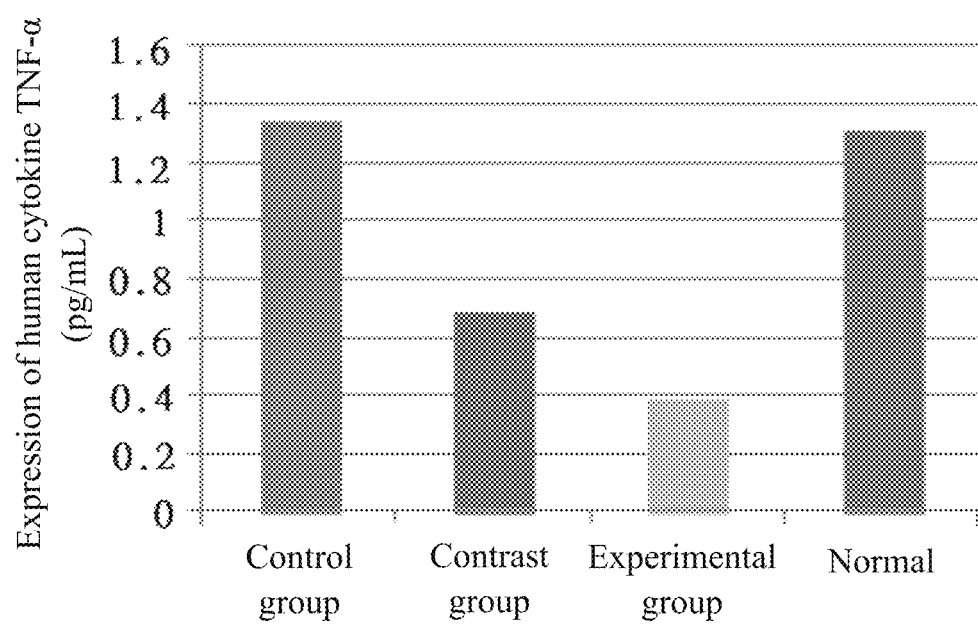
Figure 5E:
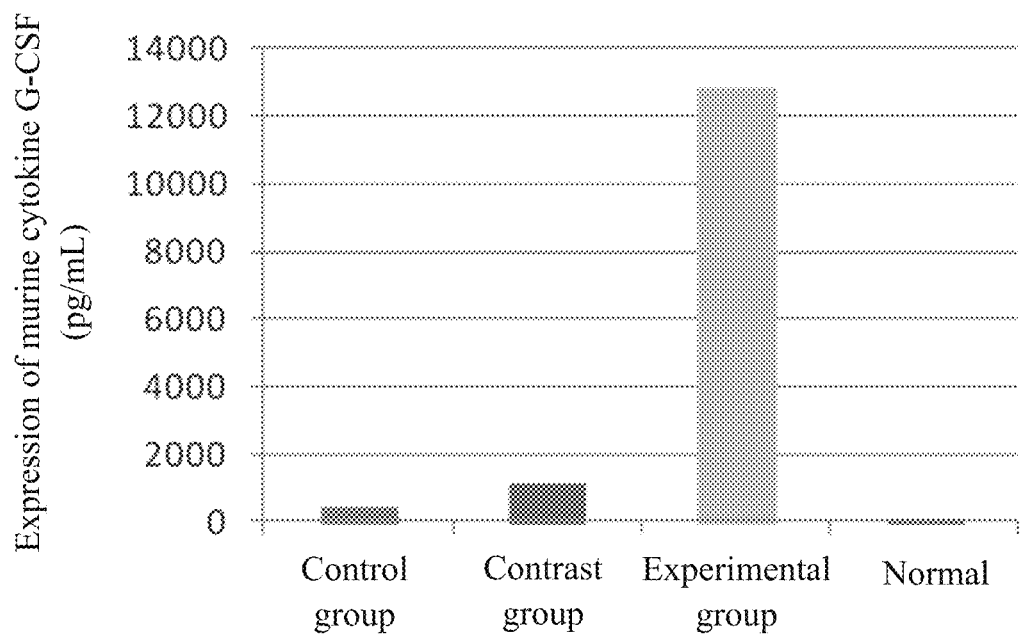
Figure 5F:
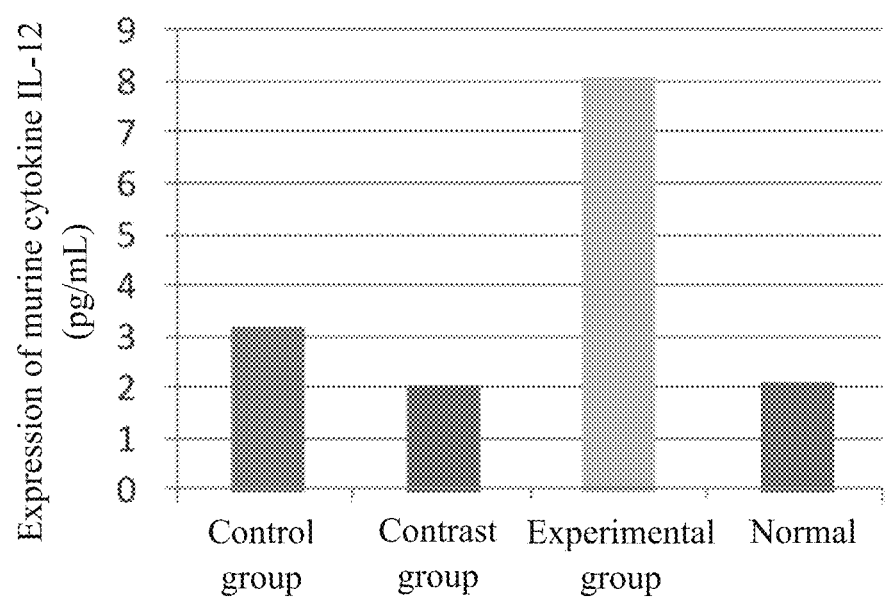
Figure 5G:
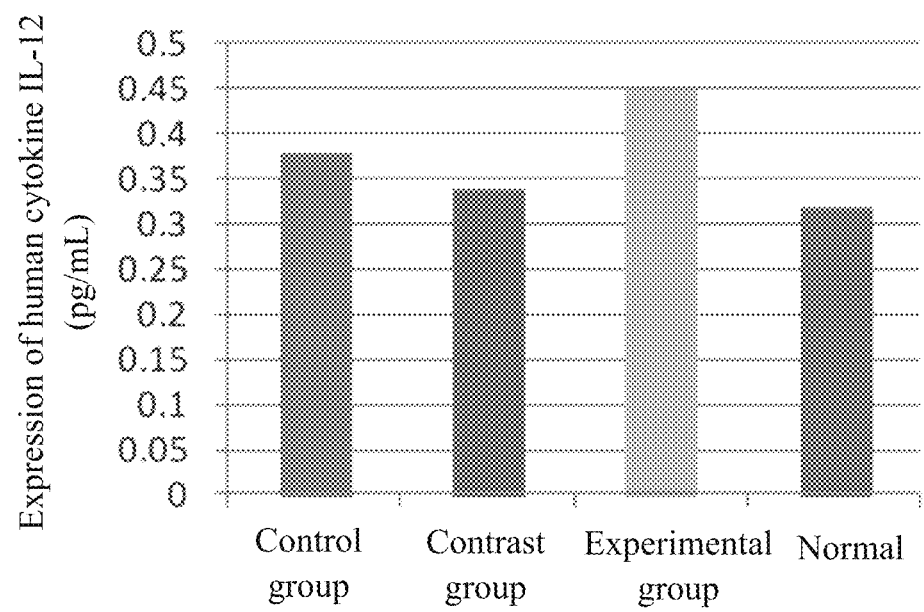

Please refer to FIGS. 5A-5E. The rats of normal group were neither implant colon cancer cells nor administered drugs. Compare with control group and contrast group, present pharmaceutical composition can decrease the expression of human cytokine IL-8 (FIG. 5A), IL-6 (FIG. 5B), IL-1RA (FIG. 5C), TNF-α (FIG. 5D), and can increase the expression of murine cytokine G-CSF (FIG. 5E), IL-12 (p70) (FIG. 5F) and human cytokine IL-12 (p70) (FIG. 5G).

Figure 6A:
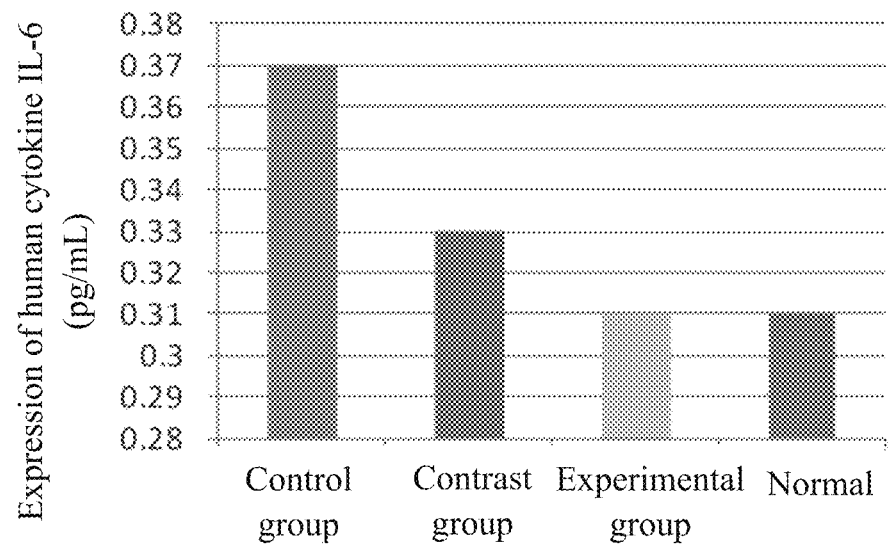
FIGS. 6A-D illustrates the expression of cytokines in the blood after implant the lung adenocarcinoma cells.
Figure 6B:
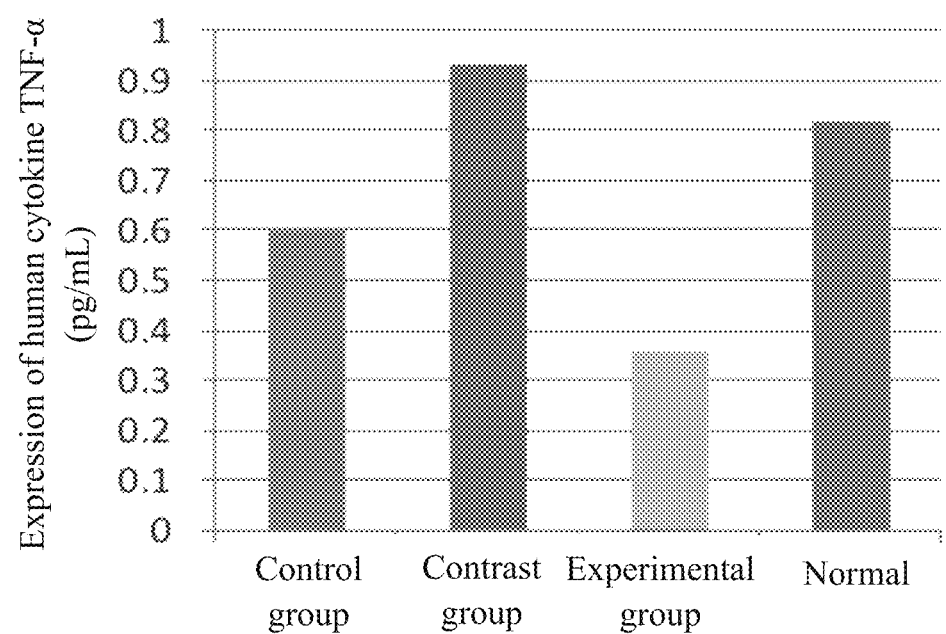
Figure 6C:
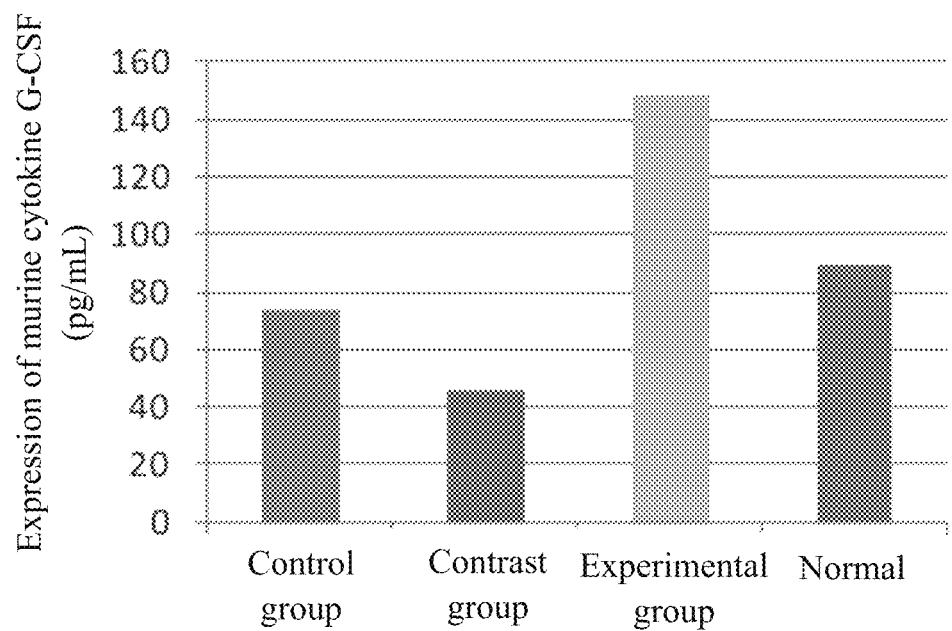
Figure 6D:
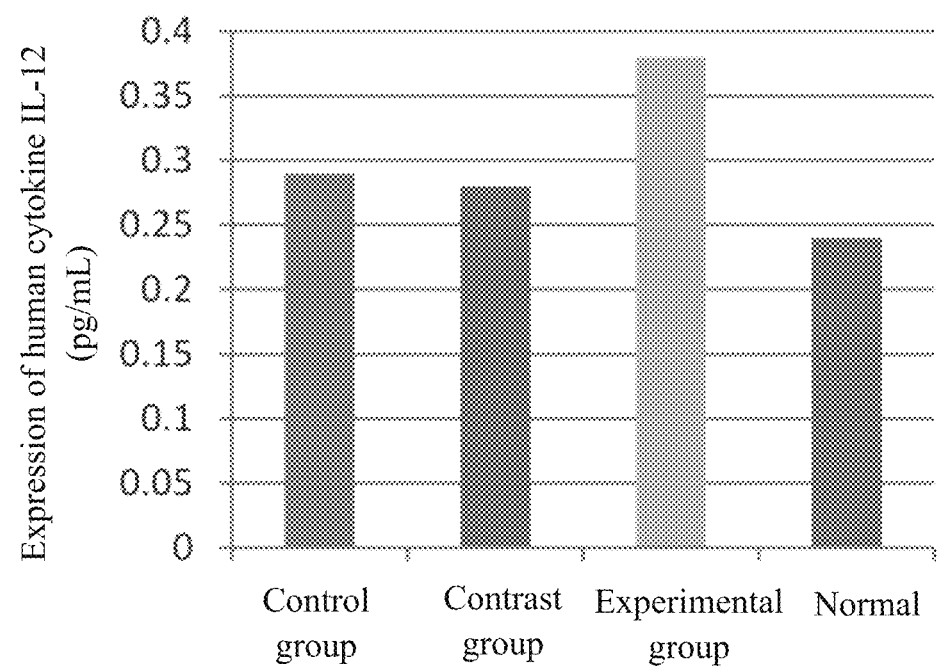

Please refer to FIGS. 6A-6D. The rats of normal group were neither implant lung adenocarcinoma nor administered drugs. Compare with normal group and control group, present pharmaceutical composition can decrease the expression of human cytokine IL-6 (FIG. 6A), TNF-α (FIG. 6B)), and can increase the expression of murine cytokine G-CSF (FIG. 6C) and human cytokine IL-12 (p70) (FIG. 6D). According to above results, the pharmaceutical compositions of the present invention have ability to improve the autoimmunity of cancer patients.

Furthermore, a common side effect of chemotherapy is a drop in the number of white blood cells, which leads to an increased risk of getting an infection. Currently, granulocyte colony stimulating factor (G-CSF) treatment can make white blood cell levels go up faster. However, patients may have one or more side effects of using G-CSF. To understand the effect of present pharmaceutical composition on white blood cells, cyclophosphamide-induced leukopenia experiment execute as follows: 6 to 7 week-old female rats (20-24 grams, ICR) were divided into normal group, disease group, contrast group and experimental group. In normal group, rats were not gave any medication. In disease, contrast and experimental group, rats were administered cyclophosphamide on day 0 to induce leukopenia. Besides, in contrast group, rats were also administered G-CSF on day 2 to day 4. In experimental group, rats were treated with presented pharmaceutical composition for 5 days before administered cyclophosphamide, and continuously treated for 10 days after administered cyclophosphamid. Therefore, the total days of presented pharmaceutical composition administered in experimental group is 15 days. The administered method of presented pharmaceutical composition is twice daily, and the dosage was 0.5-1.67 uL/mouse. The rats in each group were phlebotomized on day 0 before chemotherapy, and on day 4, day 7 and day 10 after chemotherapy.

Please refer to Table 1. Compared to normal group, the numbers of white blood cell are extremely reduced in disease group, means cyclophosphamid can induce leucopenia. In contrast group, the numbers of white blood cell increase on day 7 and day 10. However, compared to contrast group, the experimental group recover white blood cells quickly after chemotherapy. Also, the mice in experimental group not observe have any side effects. The results show that the pharmaceutical composition of the present invention is better than G-CSF, and have great positive effects on mice.

TABLE 1

| | the numbers of white blood cell | | | |
|---|---|---|---|---|
| Group | Day 0 before chemo-therapy | Day 4 after chemo-therapy | Day 7 after chemo-therapy | Day 10 after chemo-therapy |
| Normal group | 842 | 731 | 838 | 843 |
| Disease group | 887 | 56 | 333 | 772 |
| Contrast group | 843 | 51 | 528 | 768 |
| Experimental group | 818 | 63 | 633 | 1101 |

5. The Effect of the Presented Pharmaceutical Compositions on Cancer Pain

Cancer pain is a kind of pain caused by cancer, which is most common symptoms and most feared symptoms for patients. If the pain is not controlled properly, the life quality of patients would be affected severely. To understand the effect of presented pharmaceutical composition on cancer pain, the experiment was following: 6 to 7 week-old female rats (20-24 grams, ICR) were divided into control group, contrast group and experimental group. In control group, rats were not gave any medication. In contrast group and experimental group, rats were administered Taxol® (20 mg/kg) from day 0 to day 5 to induce the pain. Besides, the experimental group were also treated with presented pharmaceutical composition for 7 days before administered Taxol®, and continuously treated for 14 days after administered Taxol®. Therefore, the total days of presented pharmaceutical composition administered in experimental group is 21 days. The administered method is twice daily, and the dosage was 0.5-1.67 uL/mouse. On day 3, 7 and 14 during the drug administration, the tail flick latency (Tail-Flick Unit 37360) was conducted. The tail flick latency is used to evaluate the degree of change of pain threshold by heating the tail of rat through infrared.

Figure 7:
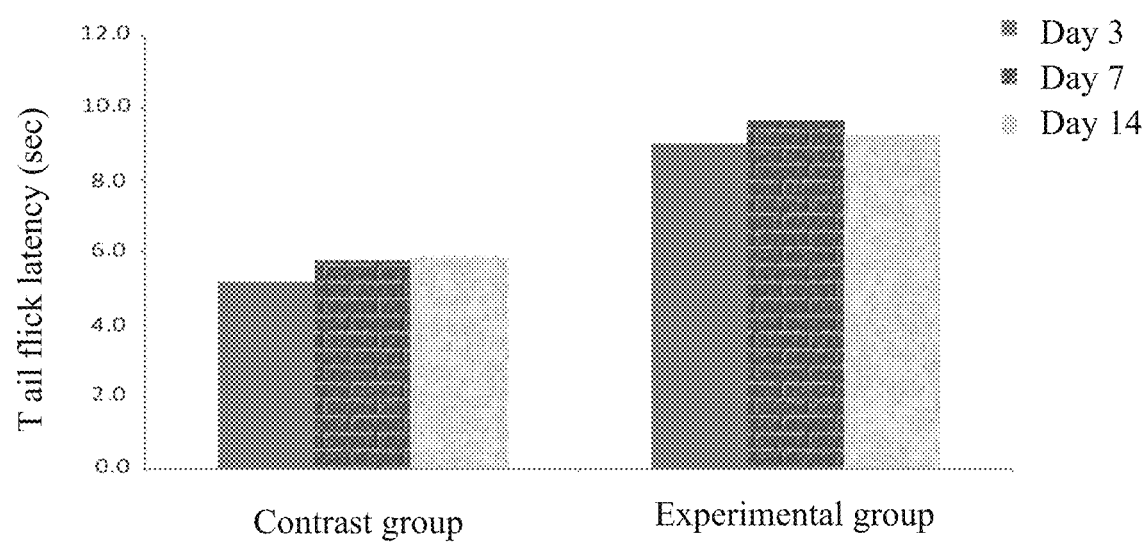
FIG. 7 illustrates the comparison of pain in different days.
Figure 8A:
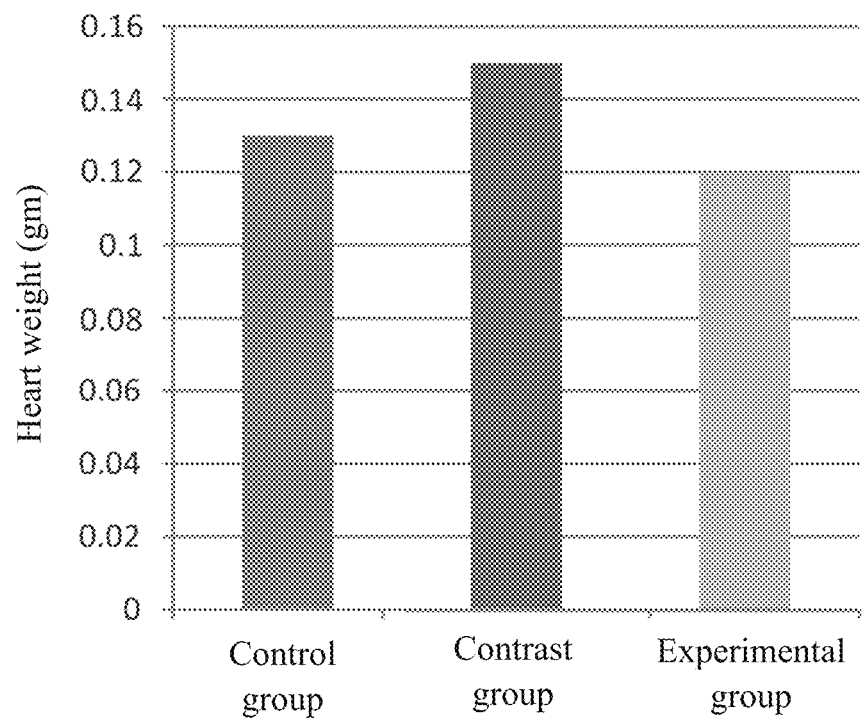
FIGS. 8A-D illustrates the organ weight of all groups.
Figure 8B:
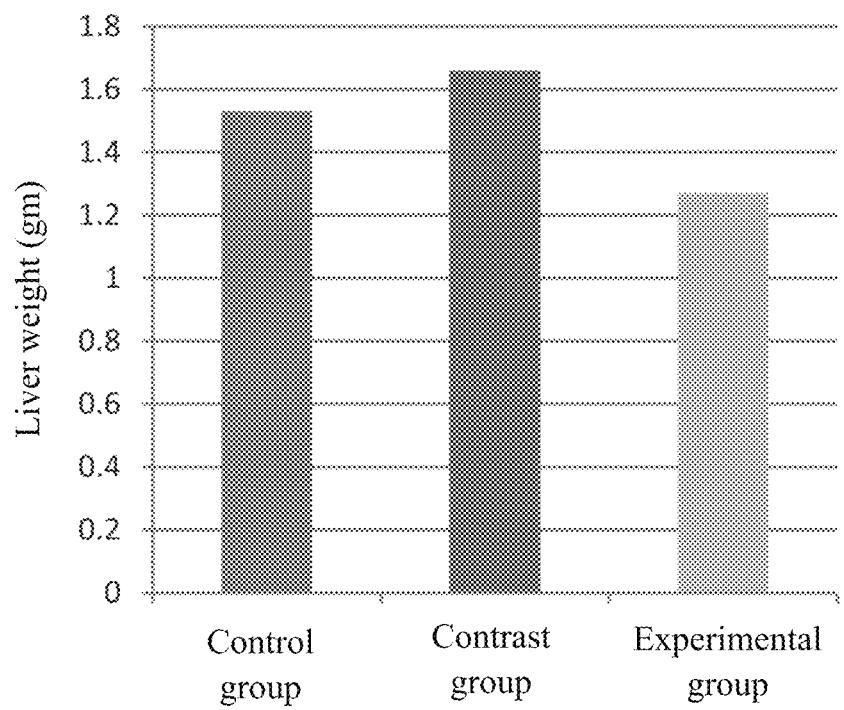
Figure 8C:
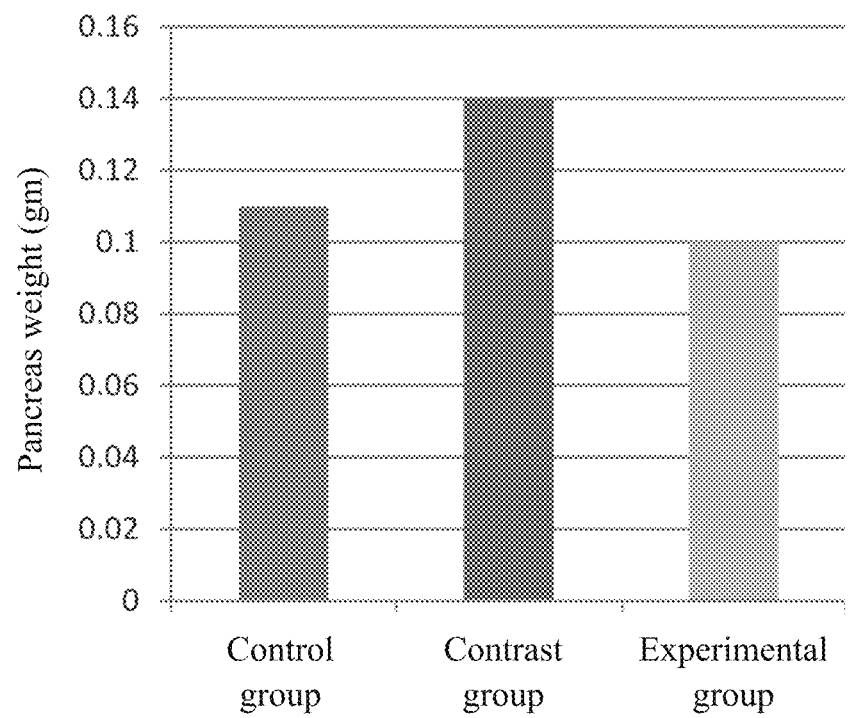
Figure 8D:
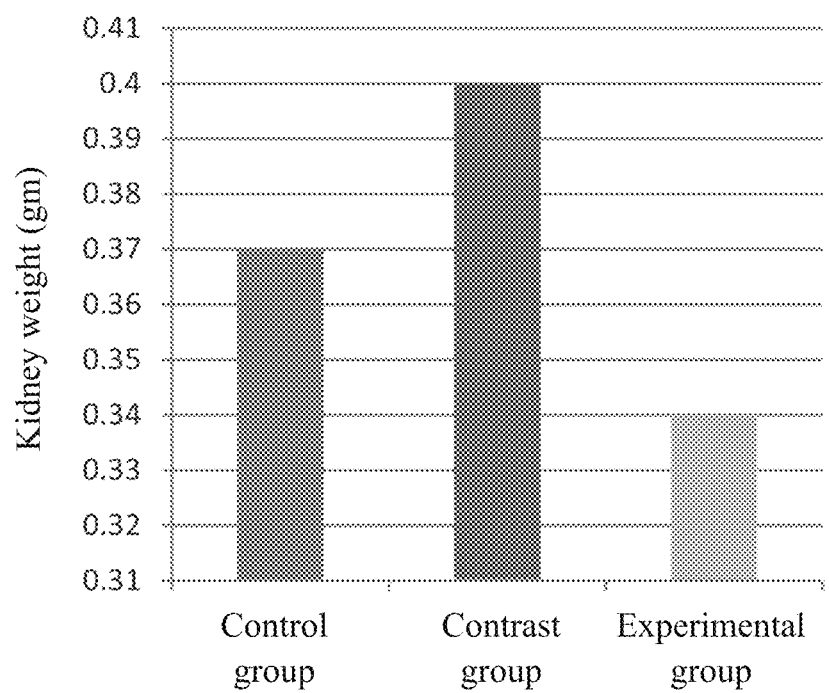

Please refer to FIG. 7. The seconds of the contrast group were lower, means Taxol® would leading increase of the pain sensitivity of rats. However, compared to contrast group, the seconds of the experimental group were increase in day 3, day 7 and day 14. Accordingly, the pharmaceutical compositions of the present invention have ability to reduce the cancer pain.

6. The Impact of Presented Pharmaceutical Compositions on Various Organs

Organ hypertrophy is common side effect induced by chemotherapy drugs. To understand the impact of the presented pharmaceutical compositions on organs, the female rats of example 5 were sacrificed on day 15. The heart, liver, spleen and kidney acquired from rats were weighted respectively.

Please refer to FIGS. 8A-8D. In contrast group, the heart (FIG. 8A), liver (FIG. 8B), spleen (FIG. 8C) and kidney (FIG. 8D) was significantly heavier than control group. However, in experimental group, the weight of heart (FIG. 8A), liver (FIG. 8B), spleen (FIG. 8C) and kidney (FIG. 8D) was significantly decreased, even lower than control group. Thus, the pharmaceutical compositions of the present invention could protect the organs from the side-effects caused by chemotherapeutic drugs.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A method for decreasing side effects of a cancer drug in a patient in need thereof, comprising:
 administering an effective amount of a pharmaceutical composition to the patient,
 wherein the pharmaceutical composition comprises:
 a mushroom component consisting of 24-36 grams of *Phellinus linteus*, 16-24 grams of *Ganoderma lucidum*, 16-24 grams of *Agaricus subrufescen*, 4-6 grams of *Antrodia cinnamomea*, 4-6 grams of *Caterpillar fungus*;
 a rhizome component consisting of 16-24 grams of *Rhizoma polygonati*, 8-12 grams of *Astragalus*, 8-12 grams of *Salvia miltiorrhiza*, 8-12 grams of *Codonopsis pilosula*, 12-18 grams of *Hedyotis diffusa*, 12-18 grams of *Eucommia ulmoides*, 8-12 grams of *Atractylodes macrocephala*, 8-12 grams of *Radix trichosanthis*, 8-12 grams of *Eleutherococcus senticosus*, 8-12 grams of *Ophiopogon japonicas*, 8-12 grams of *Rhodiola*, 2.4-3.6 grams of Peeled Licorice;
 a fruit component consisting of 12-18 grams of Job's Tears, 8-12 grams of *Ligustrum lucidum*, 8-12 grams of *Schisandra chinensis*, 9.6-14.4 grams of Germinated brown rice, 8-12 grams of lotus seed, 8-12 grams of Black sesame, 8-12 grams of Corn Silk, 8-12 grams of *Siraitiagros venorii*, 1.6-2.4 grams of powder extract from red grape skin;
 a leaf component consisting of 8-12 grams of spinach, 8-12 grams of germinated Broccoli, 8-12 grams of papaya leaf, 6.4-9.6 grams of lotus leaf;
 a flower consists component consisting of 8-12 grams of Chrysanthemum, 8-12 grams of *Cota tinctoria*, 8-12 grams of *Lonicera Japonica*, 8-12 grams of *Matricaria recutita* (Chamomile);
 an alga component consisting of 8-12 grams of seaweed, 8-12 grams of sea-tangle, 8-12 grams of kelp;
 an energy-rich liquid consisting of 4.5 to 5.5 mg of ferric chloride and 200 ml of distilled water;
 a salt-rich liquid consisting of 112.5-137.5 grams of deep sea salt, 27-33 grams of magnesium chloride, 18-22 ml of brine, 0.99-1.21 grams of calcium chloride and 0.495-0.605 grams potassium chloride;
 an assist agent consisting of 18-22 grams of citric acid, 18-22 grams of selenium yeast, 270-330 mg of coenzyme Q10 and 2.7-3.3 grams of vitamin C;
 an anti-oxide agent consisting of 9-11 grams of *chitin oligosaccharides*, 4.5-5.5 grams of glutathione, 0.9-1.1 grams of pine bark, and 0.9 -1.1 grams of Fucoidan,
 wherein the pharmaceutical composition can protect an organ from the side effects of the cancer drug, increase immunity, reduce pain, or improve the efficacy of the cancer drug, and
 wherein the cancer drug is selected form the group consisting of 5-fluorouracil (5-FU), Taxol, cisplatin, anthracycline, cyclophosphamide and a combination thereof.

2. The method of claim 1, wherein the pharmaceutical composition is administered in an amount of 25 μl/kg/day-84 μl/kg/day.

3. The method of claim 1, wherein the pharmaceutical composition is administered 3-10 times daily.

4. The method of claim 1, wherein the organ is heart, liver, kidney or pancreas.

* * * * *